(12) United States Patent
Ghosh et al.

(10) Patent No.: US 12,243,650 B2
(45) Date of Patent: Mar. 4, 2025

(54) METHOD AND SYSTEM FOR CONTACT TRACING USING POSITIONING IN A VENUE

(71) Applicant: INVENSENSE, INC., San Jose, CA (US)

(72) Inventors: Sumit Ghosh, Calgary (CA); Vijay Ramesh, Calgary (CA); Nagesh Arunarthy, Calgary (CA); Jacques Georgy, Calgary (CA); Gennadii Berkovich, Calgary (CA); Christopher Goodall, Calgary (CA); Takashi Nakayama, Calgary (CA)

(*) Notice: Subject to any disclaimer, the term of this patent is extended or adjusted under 35 U.S.C. 154(b) by 517 days.

(21) Appl. No.: 17/503,099

(22) Filed: Oct. 15, 2021

(65) Prior Publication Data
US 2022/0122738 A1 Apr. 21, 2022

Related U.S. Application Data

(60) Provisional application No. 63/092,219, filed on Oct. 15, 2020.

(51) Int. Cl.
*H04W 4/029* (2018.01)
*G06N 5/04* (2023.01)
*G16H 50/50* (2018.01)
*H04W 4/33* (2018.01)

(52) U.S. Cl.
CPC ............... *G16H 50/50* (2018.01); *G06N 5/04* (2013.01); *H04W 4/029* (2018.02); *H04W 4/33* (2018.02)

(58) Field of Classification Search
CPC .............................. G16H 50/50; H04W 4/33
USPC ....................................... 455/456.1
See application file for complete search history.

(56) References Cited

U.S. PATENT DOCUMENTS

| 8,359,643 | B2 * | 1/2013 | Low | H04L 63/08 |
| | | | | 370/254 |
| 11,342,051 | B1 * | 5/2022 | Jain | G16H 10/60 |

\* cited by examiner

*Primary Examiner* — Qutbuddin Ghulamali

(57) ABSTRACT

Systems and methods are provided for establishing contact tracing for a group of users within a venue. Position information in the venue may be estimated for each user over a period of time based at least in part on data from a portable device associated with each user. At least one contact parameter may be established so that contact between at least two users of the group of users during the period of time may be determined based at least in part on the at least one contact parameter and the estimated position information.

29 Claims, 11 Drawing Sheets

METHOD AND SYSTEM FOR CONTACT TRACING USING POSITIONING IN A VENUE

CROSS-REFERENCE TO RELATED APPLICATIONS

This application claims priority from and benefit of U.S. Provisional Patent Application Ser. No. 63/092,219, filed Oct. 15, 2020, which is entitled "Method and System for Tracing the Spread of Diseases Using Indoor Positioning," is assigned to the assignee hereof, and is incorporated by reference in its entirety.

FIELD OF THE PRESENT DISCLOSURE

This disclosure generally relates to positioning within a venue and more particularly to employing positioning information to determine contact between at least two individuals, such as for assessing the probability of spread of disease.

BACKGROUND

Contact tracing is an important technique for inhibiting the spread of infectious diseases. Given that portable electronic devices, such as a smartphone and others configured to be handheld or otherwise associated with a user, are employed in a wide variety of applications and environments, it would be desirable to utilize their ubiquity to provide contact tracing information. For example, one category of existing contact tracing solutions relies on Bluetooth Low Energy (BLE), ultrawide band (UWB) or ultrasonic techniques to detect proximity between two devices through ranging. As will be appreciated, there are certain limitations associated with these techniques. Ranging simply relies on the existence of wireless communications between the two devices. This gives relative position information for the two devices but does not provide position information with respect to the venue and therefore does not consider structures or other characteristics of the environment, such as walls, floors, dividers or other partitions. Notably, this can cause a false positive when the two devices are separated by a physical barrier that would prevent contact or transmission of a disease, but nevertheless allows wireless communication. Moreover, ranging only gives information about contemporaneous proximity and does not account for the possibility of asynchronous transmission between two individuals through a surface, object or contained environment at different times. Still further, contact tracing using ranging or other similar proximity detection is limited by hardware constraints in that the number of devices that can connect with each other at one time may be limited and the respective systems must be powered on and active. As yet another example of the challenges associated with these techniques is that distance and/or direction estimations may be relatively inaccurate. Contact tracing using other techniques such as a Global Navigation Satellite System (GNSS) may not be suitable in venues having an indoor environment due to the poor signal quality even if available at all. Accordingly, there remains a need for contact tracing, particularly within an indoor environment or other venue that overcomes these and other drawbacks as described in the following materials.

SUMMARY

As will be described in detail below, this disclosure includes methods for establishing contact tracing for a group of users within a venue. The method may involve estimating position information in the venue for each user over a period of time based at least in part on data from a portable device associated with each user, establishing at least one contact parameter and determining contact between at least two users of the group of users during the period of time based at least in part on the estimated position information and the at least one contact parameter.

Further, this disclosure includes a system for establishing contact tracing for a group of users within a venue. The system may include a portable device associated with each user, wherein each portable device comprises at least one processor configured to estimate position information based at least in part on data from the portable device, and at least one remote processor that may be configured to receive estimated position information in the venue for each user over a period of time, establish at least one contact parameter and determine contact between at least two users of the group of users during the period of time based at least in part on the estimated position information and the at least contact parameter.

In other embodiments, this disclosure includes a system for establishing contact tracing for a group of users within a venue in which the system has a portable device associated with each user and at least one remote processor configured to estimate position information in the venue for each user over a period of time based at least in part on data from the portable device of each user, establish at least one contact parameter and determine contact between at least two users of the group of users during the period of time based at least in part on the estimated position information and the at least contact parameter

DETAILED DESCRIPTION

Figure 1:
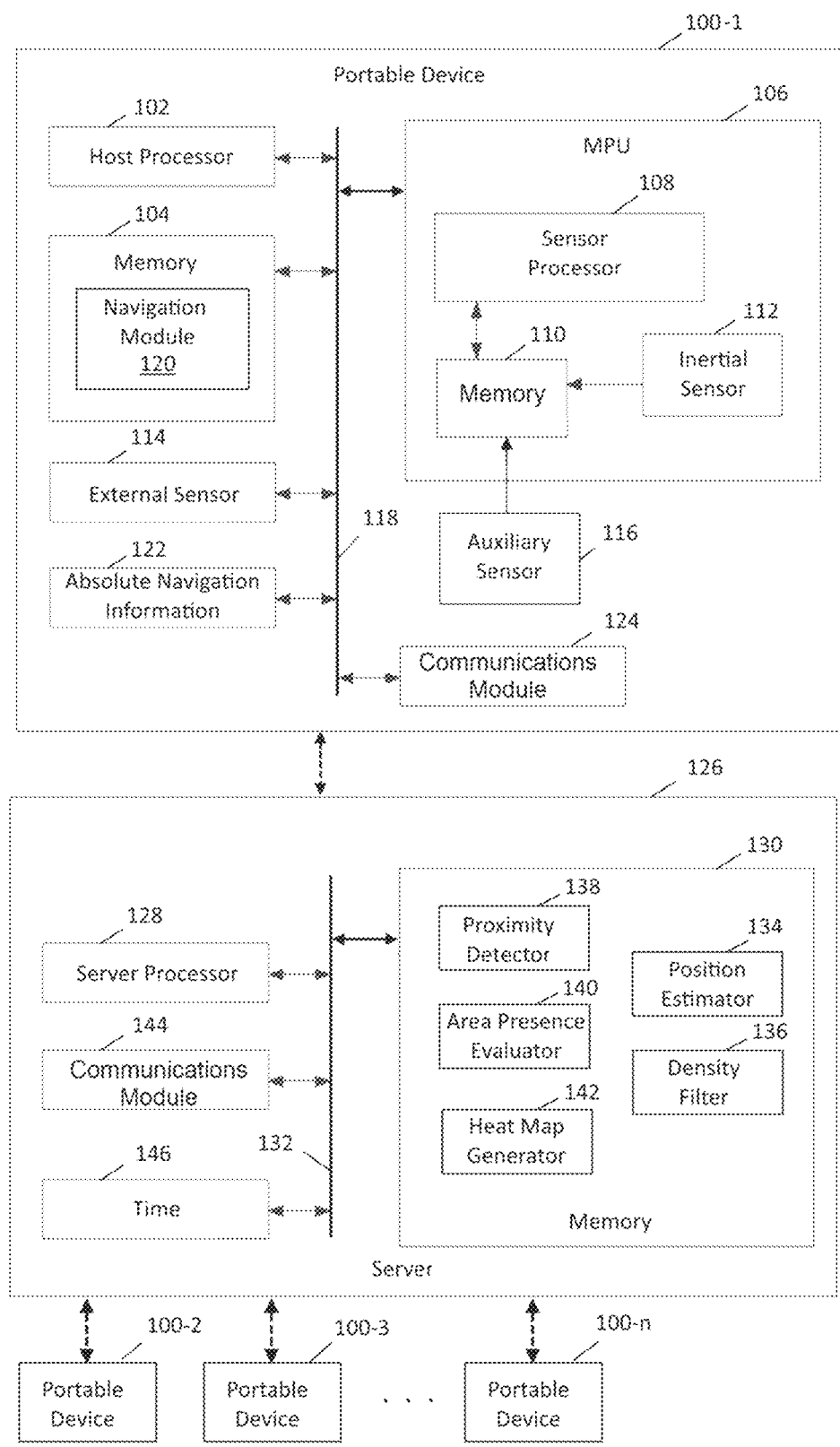
FIG. 1 is a schematic diagram of a system of establishing contact tracing according to an embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings or chip embodiments. These and similar directional terms should not be construed to limit the scope of the disclosure in any manner.

In this specification and in the claims, it will be understood that when an element is referred to as being "connected to" or "coupled to" another element, it can be directly connected or coupled to the other element or intervening elements may be present. In contrast, when an element is referred to as being "directly connected to" or "directly coupled to" another element, there are no intervening elements present.

Some portions of the detailed descriptions which follow are presented in terms of procedures, logic blocks, processing and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "accessing," "receiving," "sending," "using," "selecting," "determining," "normalizing," "multiplying," "averaging," "monitoring," "comparing," "applying," "updating," "measuring," "deriving" or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the exemplary wireless communications devices may include components other than those shown, including well-known components such as a processor, memory and the like.

The techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, performs one or more of the methods described above. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor. For example, a carrier wave may be employed to carry computer-readable electronic data such as those used in transmitting and receiving electronic mail or in accessing a network such as the internet or a local area network (LAN). Of course, many modifications may be made to this configuration without departing from the scope or spirit of the claimed subject matter.

The various illustrative logical blocks, modules, circuits and instructions described in connection with the embodiments disclosed herein may be executed by one or more processors, such as one or more motion processing units (MPUs), digital signal processors (DSPs), general purpose microprocessors, application specific integrated circuits (ASICs), application specific instruction set processors (ASIPs), field programmable gate arrays (FPGAs), or other equivalent integrated or discrete logic circuitry. The term "processor," as used herein may refer to any of the foregoing structures or any other structure suitable for implementation of the techniques described herein. In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an MPU and a microprocessor, a plurality of microprocessors, one or more microprocessors in conjunction with an MPU core, or any other such configuration.

Unless defined otherwise, all technical and scientific terms used herein have the same meaning as commonly understood by one having ordinary skill in the art to which the disclosure pertains.

Finally, as used in this specification and the appended claims, the singular forms "a," "an" and "the" include plural referents unless the content clearly dictates otherwise.

Portable electronic devices, such as those configured to be handheld or otherwise associated with a user, are employed in a wide variety of applications and environments. The ubiquity of such devices as mobile phones or smartphones, wearables, including smart watches and glasses, digital still cameras and video cameras, handheld music and media players, portable video game devices and controllers, tablets, mobile internet devices (MIDs), personal navigation devices (PNDs), and other similar devices speaks to the popularity and desire for these types of devices. Increasingly, such devices are equipped with one or more sensors and/or other systems for determining the position or motion of the portable device. For example, self-contained strategies may include dead reckoning determinations based upon the integration of specific forces and angular rates measured by inertial sensors (e.g. accelerometer, gyroscopes) integrated into the device, such as through an inertial navigation system (INS). The position estimations of this disclosure are discussed in the context of a venue, such as shopping malls, retail stores, offices, airports, hospitals, museums, theatres, government buildings, parking complexes and other defined areas. Notably, the venue may be characterized as having one or more indoor environments that may limit or degrade the availability of satellite-based positioning. For example, a shopping mall may have outdoor paths connecting multiple indoor stores. Desirably, map information is available for the venue and may be used in multiple ways.

As will be described below, position information can also be estimated using fingerprinting of electromagnetic fields, such as Wi-Fi fingerprinting, magnetic fingerprinting, Bluetooth fingerprinting and others. Position information can also be estimated using map matching to compare physical characteristics of the environment to obtain map information. Yet another example of information that can be used in position estimation, if available, is derived from infrastructure beacons, such as radio frequency identification (RFID), Bluetooth, optical-based beacons (e.g. visible light communication (VLC)) or alternatives. A further optional source of position information is collaborative assistance data received from neighboring peer devices. Other navigational techniques may also be used, including reference-based strategies including satellite-based navigation, such as a Global Navigation Satellite System (GNSS), and signal trilateration using wireless local area networks (WLANs) or cellular telecommunication systems, but signal attenuation within indoor environments may limit their suitability. Although estimating position information may involve determining a full navigation solution including position, velocity and attitude or a partial navigation solution of position and attitude, at a minimum position information is provided with respect to the venue. Still further, position information can be augmented with determinations made using ranging techniques between peer devices, which may employ any suitable wireless communication protocol such as Bluetooth Low Energy (BLE), ultrawide band (UWB), or others, as well as other technologies such as ultrasonic. Since ranging gives a relative position with respect to other devices, it is not directly a position estimation in the venue according to the techniques of this disclosure These and other aspects of this disclosure may be appreciated in the context of FIG. 1, which depicts features of a suitable portable device 100-1 with high level schematic blocks. As shown, device 100-1 includes a host processor 102, which may be one or more microprocessors, central processing units (CPUs), or other processors to run software programs, which may be stored in memory 104, associated with the functions of device 100. Multiple layers of software can be provided in memory 104, which may be any combination of computer readable medium such as electronic memory or other storage medium such as hard disk, optical disk, etc., for use with the host processor 102. For example, an operating system layer can be provided for device 100-1 to control and manage system resources in real time, enable functions of application software and other layers, and interface application programs with other software and functions of device 100-1. Similarly, different software application programs such as menu navigation software, games, camera function control, navigation software, communications software, such as telephony or wireless local area network (WLAN) software, or any of a wide variety of other software and functional interfaces can be provided. In some embodiments, multiple different applications can be provided on a single device 100-1, and in some of those embodiments, multiple applications can run simultaneously.

Device 100-1 includes at least one sensor assembly, as shown here in the form of integrated motion processing unit (MPU™) 106 featuring sensor processor 108, memory 110 and inertial sensor 112. Memory 110 may store algorithms, routines or other instructions for processing data output by inertial sensor 112 and/or other sensors as described below using logic or controllers of sensor processor 108, as well as storing raw data and/or motion data output by inertial sensor 112 or other sensors. Inertial sensor 112 may be one or more sensors for measuring motion of device 100-1 in space. Depending on the configuration, MPU 106 measures one or more axes of rotation and/or one or more axes of acceleration of the device. In one embodiment, inertial sensor 112 may include rotational motion sensors or linear motion sensors. For example, the rotational motion sensors may be gyroscopes to measure angular velocity along one or more orthogonal axes and the linear motion sensors may be accelerometers to measure linear acceleration along one or more orthogonal axes. In one aspect, three gyroscopes and three accelerometers may be employed, such that a sensor fusion operation performed by sensor processor 108, or other processing resources of device 100, combines data from inertial sensor 112 to provide a six axis determination of motion. As desired, inertial sensor 112 may be implemented using Micro Electro Mechanical System (MEMS) to be integrated with MPU 106 in a single package. Exemplary details regarding suitable configurations of host processor 102 and MPU 106 may be found in co-pending, commonly-owned U.S. Pat. Nos. 8,250,921 and 8,952,832, which are hereby incorporated by reference in their entirety. Suitable implementations for MPU 106 in device 100-1 are available from InvenSense, Inc. of Sunnyvale, Calif.

Alternatively or in addition, device 100-1 may implement a sensor assembly in the form of external sensor 114. This is optional and not required in all embodiments. External sensors may represent one or more sensors as described above, such as an accelerometer and/or a gyroscope, which output data for use in deriving a navigation solution. As used herein, "external" means a sensor that is not integrated with MPU 106 and may be remote or local to device 100. Also alternatively or in addition, MPU 106 may receive data from an auxiliary sensor 116 configured to measure one or more aspects about the environment surrounding device 100-1. This is optional and not required in all embodiments. For example, a barometer and/or a magnetometer may be used to refine position determinations made using inertial sensor 112. In one embodiment, auxiliary sensor 116 may include a magnetometer measuring along three orthogonal axes and output data to be fused with the gyroscope and accelerometer inertial sensor data to provide a nine axis determination of motion. In another embodiment, auxiliary sensor 116 may also include a barometer to provide an altitude determination that may be fused with the other sensor data to provide a ten axis determination of motion. Although described in the context of one or more sensors being MEMS based, the techniques of this disclosure may be applied to any sensor design or implementation.

In the embodiment shown, host processor 102, memory 104, MPU 106 and other components of device 100-1 may be coupled through bus 118, which may be any suitable bus or interface, such as a peripheral component interconnect express (PCIe) bus, a universal serial bus (USB), a universal asynchronous receiver/transmitter (UART) serial bus, a suitable advanced microcontroller bus architecture (AMBA) interface, an Inter-Integrated Circuit (I2C) bus, a serial digital input output (SDIO) bus, a serial peripheral interface (SPI) or other equivalent. Depending on the architecture, different bus configurations may be employed as desired. For example, additional buses may be used to couple the various components of device 100-1, such as by using a dedicated bus between host processor 102 and memory 104.

In one aspect, the various operations of this disclosure used to estimate position information for portable device 100-1 may be implemented through navigation module 120 as a set of suitable instructions stored in memory 104 that may be read and executed by host processor 102. Navigation module 120 may employ a reference-based strategy, a self-contained strategy, or any combination of strategies to provide any desired degree of location awareness capabilities. For example, navigation module 120 may employ inertial navigation techniques utilizing sensor data, such as from inertial sensor 112 and/or external sensor 114, as obtained for a current sensor epoch to derive a navigation solution for that epoch which, as noted above, involves at least a position determination with respect to the venue where portable device 100-1 is located. Such techniques may involve dead reckoning or the like, and may determine an orientation for device 100-1, including values such as any roll, pitch, and azimuth (heading) angles. The navigation solutions derived by navigation module 120 represent contemporaneous determinations of position information for portable device 100-1. Although some transmission, some possible buffering, and processing time may be required, the results are at least near real time (there could be some possible latencies) and may use any information available up until the time the navigation solution is derived. Accordingly, portable device 100-1 may also have a communications module 122 supporting one or more wireless communication protocols for transmitting and/or receiving information, including position estimations derived by navigation module 120. Depending on the embodiment, communication module 122 can also be used for ranging determinations, receiving map information for map matching, communicating with infrastructure beacons, In some embodiments, navigation module 120 may employ a real-time map matching routine to aid the derivation of navigation solutions in a causal manner. Alternatively or in addition, navigation module 120 may estimate position information using "fingerprinting," by relying on recording patterns of electromagnetic signals at known locations within an area for which position information may be desired. When device 100-1 subsequently measures a pattern of received signals that is correlated with a known location, that location may be used to determine the position of the device and/or to aid another positioning technique, such as through integration with the INS techniques noted above. A suitable example of signals that may be used for fingerprinting may be based on the communication signals for an IEEE 802.11 Wireless Local Area Network (WLAN), commonly referred to as "WiFi." However, many different electromagnetic signals are suitable for location determinations using fingerprinting, including other wireless communication signals such as Bluetooth™ and radiofrequency identification (RFID). Still further, usage of environmental signals such as variations in the Earth magnetic field, such as those created by ferrous materials of buildings construction, is infrastructure-free and benefits from the long-term stability of magnetic fields within buildings. Navigation module 120 may also optionally employ other position estimation techniques as discussed above, including map matching, ranging determinations, infrastructure beacons and/or collaborative assistance data from neighboring devices.

Navigation module 120 may also use a source of absolute navigation information 124, such as a Global Navigation Satellite System (GNSS) receiver, including without limitation the Global Positioning System (GPS), the Global Navigation Satellite System (GLONASS), Galileo and/or Beidou, as well as WiFi™ positioning, cellular tower positioning, Bluetooth™ positioning beacons or other similar methods when deriving a navigation solution. This is optional and not required in all embodiments. Navigation module 120 may also be configured to use information from a wireless communication protocol to provide a position determination using signal trilateration. Any suitable protocol, including cellular-based and wireless local area network (WLAN) technologies such as Universal Terrestrial Radio Access (UTRA), Code Division Multiple Access (CDMA) networks, Global System for Mobile Communications (GSM), the Institute of Electrical and Electronics Engineers (IEEE) 802.16 (WiMAX), Long Term Evolution (LTE), IEEE 802.11 (WiFi™) and others may be employed. Further, portable device 100-1 may also have a communications module 122 for transmitting and/or receiving information, including position estimations derived by navigation module 120.

Multiple layers of software may be employed as desired and stored in any combination of memory 104, memory 110, or other suitable location. For example, a motion algorithm layer can provide motion algorithms that provide lower-level processing for raw sensor data provided from the motion sensors and other sensors. A sensor device driver layer may provide a software interface to the hardware sensors of device 100. Further, a suitable application program interface (API) may be provided to facilitate communication between host processor 102 and MPU 106, for example, to transmit desired sensor processing tasks.

In this exemplary system, portable device 100-1 communicates raw sensor data or estimated position information to server 126, which may then perform a contact tracing routine according to the techniques of this disclosure using either or both the sensor data and estimated position from portable device 100. As indicated, server 126 may also receive raw sensor data or estimated position information from additional portable devices 100-2-100-n. One suitable architecture of server 126 is depicted using high level schematic blocks in FIG. 1, and may include server processor 128 that is in communication with memory 130 over bus 132. As will be described in further detail below, server processor 128 may execute instructions stored in memory 130 that are represented as functional blocks, including position estimator 134, density filter 136, proximity detector 138, area presence evaluator 140 and heat map generator 142.

Position estimator 134 may use either or both the position estimations or the raw sensor data from each of portable devices 100-1-100-n. Notably, one or more means may be used for estimating position information including inertial motion sensor techniques, map matching techniques, fingerprinting techniques, ranging techniques, collaborative assistance data techniques, infrastructure beacon techniques, and other reference-based techniques. As discussed above, the navigation module 120 of each portable device may use any one or any combination of these techniques for estimating position. However, position estimator 134 can also be used for implementing any or all of these techniques. For example, position estimator 134 can receive sensor data from one or more portable devices 100-1-100-n and perform an inertial motion technique such as dead reckoning to determine position estimations. As desired, position estimator 134 can implement any of the other techniques and any suitable division of responsibility between navigation module 120 and position estimator 134 can be employed. Any one or combination of filters may be used to obtain the position estimates, including without limitation Kalman filters, unscented Kalman filters, particle filters and the like. Different system and measurement models can be also used according to the applications, for example: prediction only, near constant velocity and others. These models may employ different techniques to propagate the position of portable device 100 and to use navigation solution outputs as measurement updates. Thus, either or both navigation module 120 and position estimator 134 can use any one or any combination of the noted techniques to estimate positions for portable devices 100-1-100-n over time. This history of positions represents the trajectory of each device through the venue.

Further, density filter 136 may be configured to receive the position estimations for each of portable devices 100-1-100-n and provide calculations regarding the number of users per unit area in order to infer whether potential contact has occurred between two or more users. Alternatively or in addition, proximity detector 138 may also be configured to receive the position estimations for each of portable devices 100-1-100-n to determine potential contacts based at least in part on distances determined from the position estimations. Area presence evaluator 140 may be used to refine contact determinations based on characteristics of the venue determined from map information, such as whether users were in the same confined area or whether a physical barrier prevented a contact inferred from distance alone. Heat map generator 142 may be used to identify areas within the venue that have been occupied by a given user. Each of these aspects are described in further detail with respect to various embodiments in the example section below.

Server 126 may also include a communications module 144 to receive raw sensor data or navigation solutions for portable devices 100-1-100-n derived by navigation modules 120, and if desired, may transmit information related to the contact tracing back to the devices or another destination. Communications between portable devices 100-1-100-n and server 126 may employ any suitable protocol. For example, a shorter range, low power communication protocol such as BLUETOOTH®, ZigBee®, ANT or a wired connection may be used or a longer range communication protocol, such as a transmission control protocol, internet protocol (TCP/IP) packet-based communication, accessed using a wireless local area network (WLAN), cell phone protocol or the like may be used. In general, the system depicted in FIG. 1 may embody aspects of a networked or distributed computing environment. Portable devices 100-1-100-n and server 126 may communicate either directly or indirectly, such as through multiple interconnected networks. As will be appreciated, a variety of systems, components, and network configurations, topologies and infrastructures, such as client/server, peer-to-peer, or hybrid architectures, may be employed to support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any network infrastructure can be used for exemplary communications made incident to the techniques as described in various embodiments.

As noted, portable devices 100-1-100-n may derive position estimations and server 126 may perform contact tracing routines using the estimated positions. However, any or all of the functions described as being performed may be performed by any number of discrete devices in communication with each other, or may be performed by portable device 100-1 itself in other suitable system architectures. Accordingly, it should be appreciated that any suitable division of processing resources may be employed whether within one device or among a plurality of devices. Further, aspects implemented in software may include but are not limited to, application software, firmware, resident software, microcode, etc., and may take the form of a computer program product accessible from a computer-usable or computer-readable medium providing program code for use by or in connection with a computer or any instruction execution system, such as host processor 102, sensor processor 108, server processor 128, a dedicated processor or any other processing resources of portable device 100, server 126 or other remote processing resources, or may be implemented using any desired combination of software, hardware and firmware.

Map information 146 is provided as an input to server 126 and may initially be obtained from any suitable source, such as from on-line map service providers. As necessary, the map information may be preprocessed into a form suitable for use, such as by area presence evaluator 140 and/or map matching by navigation module 120 or position estimator 134. For example, the map information may be converted into an internal map data structure, where it may be saved into the local storage for future use without the overhead of downloading and processing it again if desired. Accordingly, preprocessing the map information may include the functions of i) converting map information from various map data providers to a unified data structure, ii) preparing the necessary map data structure suitable for map aided algorithms, and/or iii) storing the map information in local storage, such as memory 130 (for embodiments in which map matching is performed remotely by server 126) or memory 104 (for embodiments in which map matching is performed locally by one of portable devices 100-1-100-n).

As indicated in FIG. 1, time 148 is also used by server 126 to align the position estimations of portable devices 100-1-100-n temporally. By maintaining a history of the positions of portable devices 100-1-100-n, contact tracing can be determined on multiple bases using one or more contact parameters. For example, contact may be inferred between two users when the position estimations for their associated portable devices are within a suitable distance threshold at a given instant. Other contact parameters can also be employed, such as by establishing a threshold time interval during which the users were within a threshold distance. These parameters can be adjusted to reflect the dynamics of the potential contact. Notably, it may be desirable to employ a relatively shorter threshold time interval when the two users are determined to be relatively closer to each other. Correspondingly, a relatively longer threshold time interval may be employed when the positions of the users are relatively further apart. Further, timing is also important for other types of contact that can be determined using the techniques of this disclosure. For example, contact between users may result from a common interaction with one or more other users or an asset within the venue. As used herein, asset refers to a fixed characteristic of the environment through which disease can potentially spread. Common examples include surfaces and equipment. Maintaining a history of positions of portable devices 100-1-100-n allows for determining contact based on common interactions by evaluating when the events occurred, which can be interpreted using contact parameters such as those discussed above regarding threshold distances and/or threshold time intervals, with the estimated position information of the portable device used to infer contact with nearby surfaces or other assets. As an illustration, a first threshold time interval may be employed when evaluating the initial interaction to assess whether there was sufficient time to contaminate asset or individual and a second threshold time interval may be employed when evaluating the subsequent interaction to assess whether there was sufficient time to be contaminated.

Figure 2:
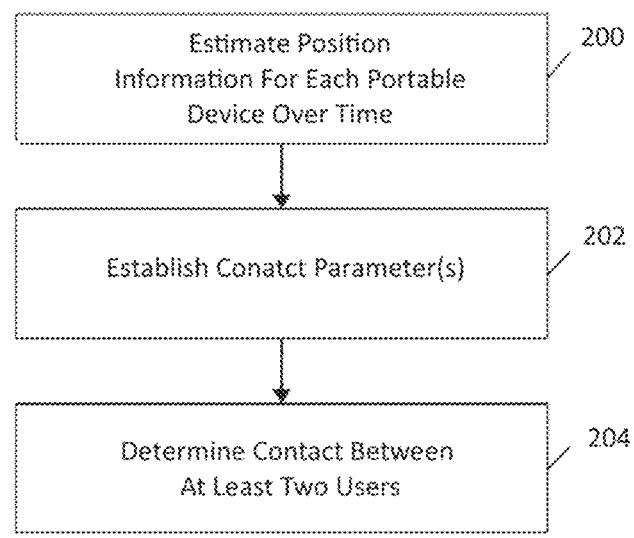
FIG. 2 is a schematic representation of an exemplary routine for establishing contact tracing according to an embodiment.

A representative routine involving the techniques of this disclosure to provide contact tracing for a group of users within a venue is depicted in FIG. 2. Beginning with 200, position information in the venue may be estimated for each user over a period of time, based at least in part on a portable device associated with each user. In 202, at least one contact parameter is established. Correspondingly, contact may be determined between at least two users based at least in part on the position information and the established contact parameter in 204.

In one aspect, the at least one contact parameter may be any one or any combination of at least one threshold distance for inferring contact and at least one threshold time interval for inferring contact.

In one aspect, determining a contact between the at least two users may be further based on a density computed using machine learning.

In one aspect, determining a contact between the at least two users may be further based on a Haversine distance between the two users.

In one aspect, determining a contact between the at least two users may be further based on common interaction with an asset within the venue.

In one aspect, determining a contact between the at least two users may be further based on common interaction with another user of the group of users.

In one aspect, map information for the venue may be obtained. Determining contacts between the at least two users may be based at least in part on the physical characteristics of the venue derived from the map information. At least one confined area may be identified, such that determining a contact between the at least two users may be further based on collocation of the two users in the identified confined area.

In one aspect, the estimated position information may be based at least in part on motion sensor data from at least one of the portable devices. The estimated position information may be further based at least in part on at least one of: i) a magnetic fingerprint; ii) a Wi-Fi fingerprint; iii) Bluetooth proximity; iv) a Bluetooth fingerprint; v) map matching; and vi) other absolute positioning systems.

In one aspect, determining a contact between the at least two users may be further based on a ranging proximity between the portable devices associated with the two users. The ranging proximity may be based on Bluetooth Low Energy communication.

In one aspect, determining a contact between the at least two users may be further based on heatmaps for each of the at least two users as determined from the position information.

In one aspect, determining a contact between the at least two users may be further based on trajectories of each of the two users as determined from the position information. The trajectories of the at least two users may indicate cross traffic flow.

In one aspect, a probability of disease spread between two users for which a contact has been determined may be estimated.

These disclosures are also directed to a system for establishing contact tracing for a group of users within a venue. The system may include a portable device associated with each user, wherein each portable device may have at least one processor configured to estimate position information based at least in part on data from the portable device, and at least one remote processor configured to receive estimated position information in the venue for each user over a period of time, establish at least one contact parameter and determine contact between at least two users of the group of users during the period of time based at least in part on the estimated position information and the at least contact parameter. Alternatively, the system may include a portable device associated with each user and at least one remote processor configured to estimate position information in the venue for each user over a period of time based at least in part on data from the portable device of each user, establish at least one contact parameter and determine contact between at least two users of the group of users during the period of time based at least in part on the estimated position information and the at least contact parameter In one aspect, the at least one remote processor may be configured to receive map information for the venue, such that determining contact between at least two users may be further based on the map information.

In one aspect, the at least one contact parameter may be any one or any combination of at least one threshold distance for inferring contact and at least one threshold time interval for inferring contact.

In one aspect, the estimated position information may be based at least in part on motion sensor data.

In one aspect, the estimated position information may be further based at least in part on at least one of a magnetic fingerprint, a Wi-Fi fingerprint, Bluetooth proximity, a Bluetooth fingerprint, map matching and other absolute positioning systems.

In one aspect, each portable device associated with at least two users further may have a ranging module, such that determining a contact between the at least two users may be further based on a ranging proximity.

EXAMPLES

Figure 3:
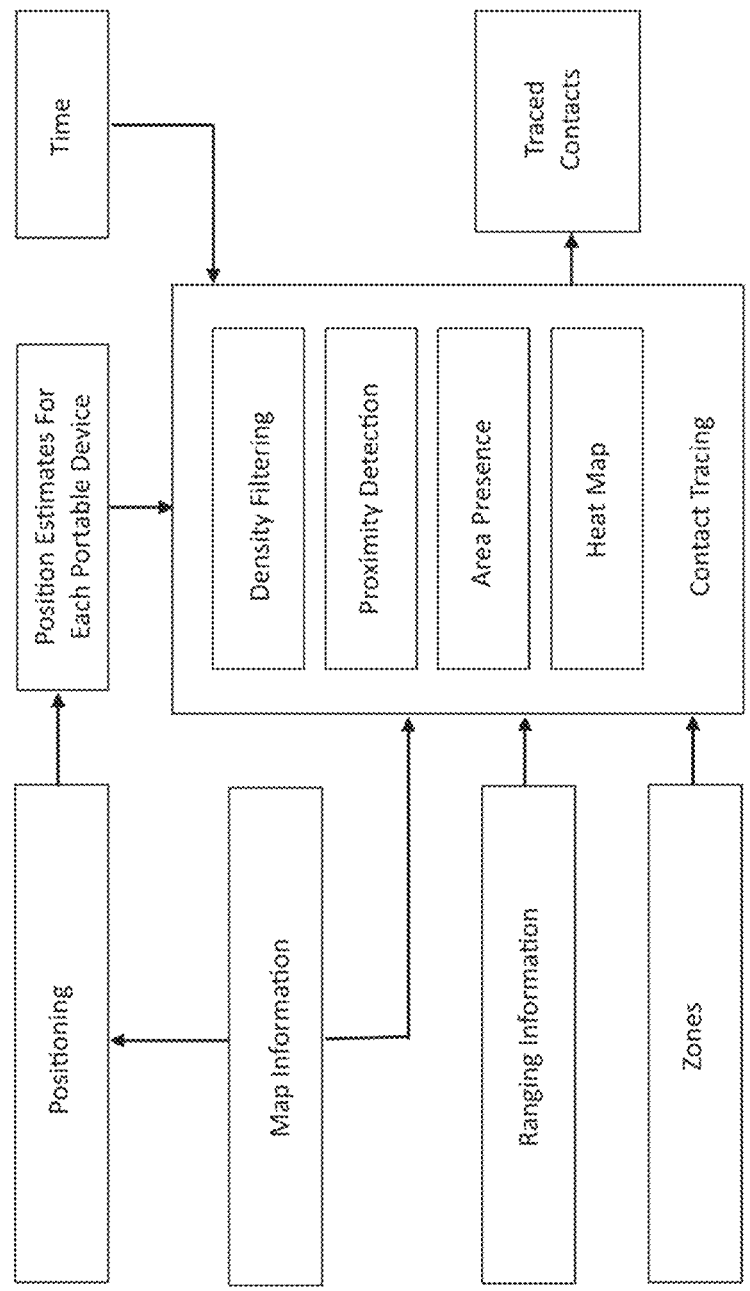
FIG. 3 is a schematic diagram of a system architecture for establishing contact tracing according to an embodiment.

To help illustrate aspects of this disclosure, an exemplary system architecture is depicted in FIG. 3. As indicated, a main input to the contract tracing routine is the position estimates for each portable device, which are temporally aligned using the time input. The position estimates can be made remotely by server 126, locally by the navigation module 120 of one or more portable devices 100-1-100-*n*, or jointly with any division of operations allocated between server 126 and portable devices 100-1-100-*n*. Further, map information may be used as an input to positioning, such as in map matching as discussed above, and/or as an input to the contact tracing routine, such as to provide relevant physical characteristics of the venue that may be used for evaluation of area presence and/or heat map generation. Map information may also be used to refine contact determination, such as by determining whether a physical barrier prevents contact that would otherwise be indicated by the position estimations. Another optional input to the contact tracing routine is ranging information that provides relative position information with respect to two devices. One suitable implementation is discussed below in the context of BLE ranging, but any suitable technology may be used to help compensate for uncertainty in position estimations. Notably, a contact determined based on position estimations can be confirmed or excluded by a ranging determination regarding the proximity of the devices. Thus, it should be appreciated that ranging information may be used as discussed previously to aid the position estimation for the portable devices but it may also be used, in addition or alternatively, as a direct input to assess a contact determination made based on the position estimations. Zones are another input to the contact tracing routine to provide context for the map information, for example by identifying confined areas, directional traffic flows or other relevant characteristics. As discussed above with regard to FIG. 1, one embodiment of a contact tracing routine may include blocks for density filtering, proximity detection, area presence and/or heat maps. Each of these is discussed in further detail below.

Figure 4A:
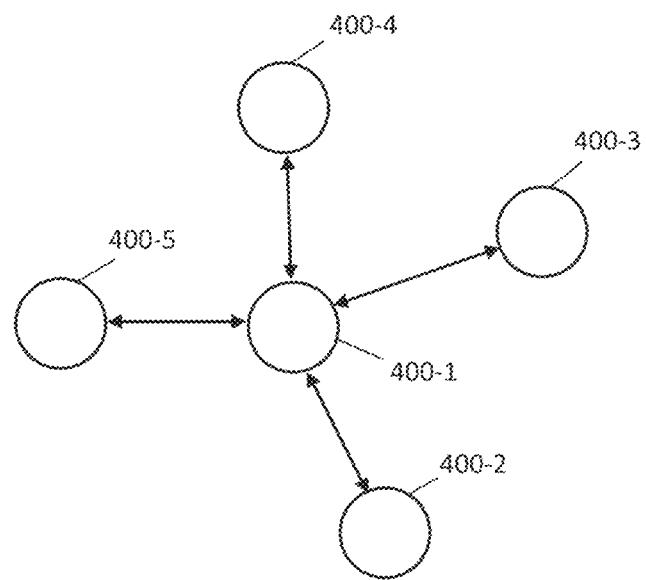
FIGS. 4A and 4B are schematic representations of Bluetooth Low Energy topologies for providing ranging information used for establishing contact tracing according to an embodiment.
Figure 4B:
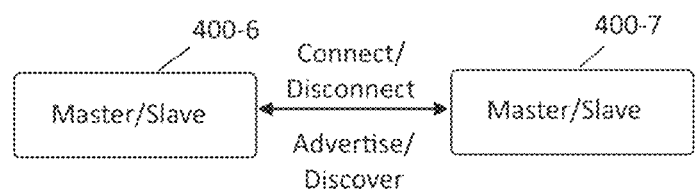
Figure 5:
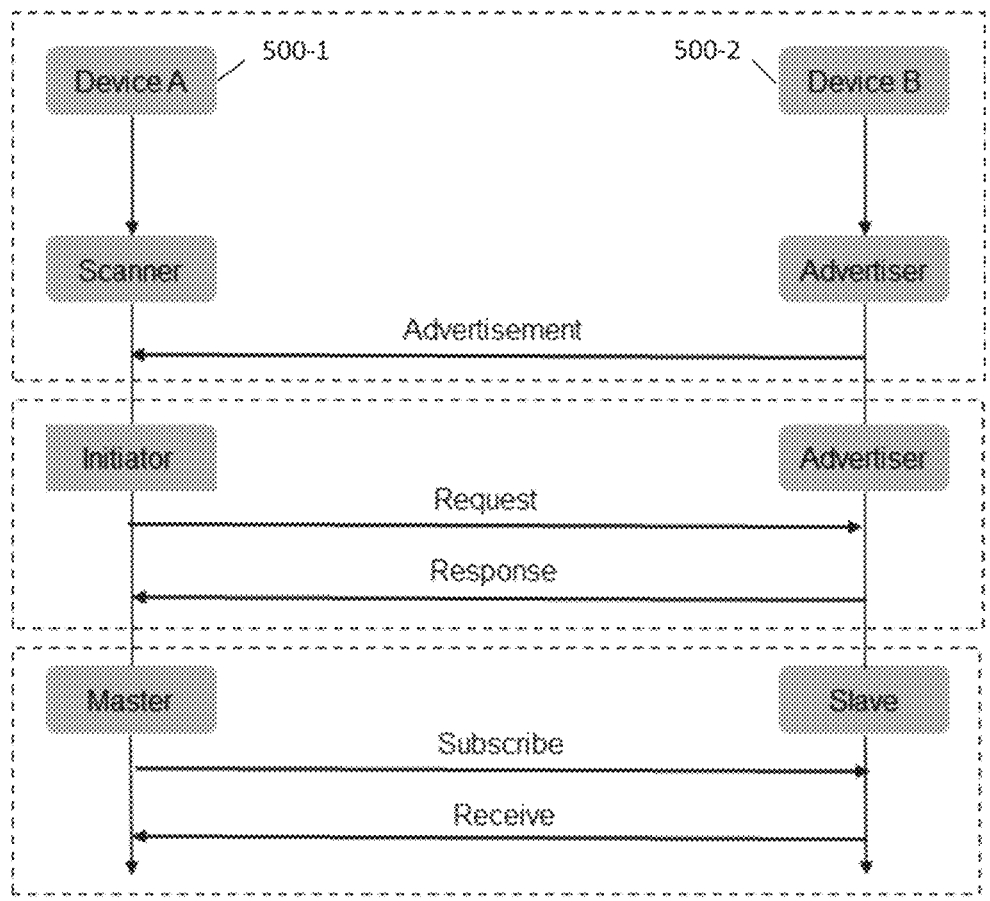
FIG. 5 is a schematic representation of Bluetooth Low Energy communication exchanges for establishing contact tracing according to an embodiment.

As noted above, one possible input used for the contact tracing determination is ranging information as determined between peer portable devices. The following example is discussed in the context of BLE ranging, which may be implemented in a star topology according to FIG. 4A, in which one portable device 400-1 acts as a master to connect with multiple other portable devices 400-2-400-5 as slaves, or in a peer to peer (P2P) topology according to FIG. 4B, in which portable devices 400-6 and 400-7 act as both master and slave. An example of communication between devices is schematically illustrated in FIG. 5, showing device 500-1 operating in a master role to discover advertising devices, connect and then subscribe to one or more slave devices 500-2. Conversely, device 500-2 operating in a slave role advertises, connects to master device 500-1 in response to a request and publishes data, communicating it to the master. The exemplary protocol depicted in FIG. 5 correspondingly has three phases. During the discovery phase, device 500-1 scans for advertisements from neighboring devices, such as device 500-2. In the connecting phase, device 500-1 then functions as an initiator, sending a request to device 500-2 after discovering its advertisement. Advertising device 500-2, sends a response after receiving the request to form the communication link. Finally, in the connected phase, master device 500-1 subscribes to slave device 500-2 in order to receive data published by slave device 500-2. Ranging information can be derived from measurements of signal strength, such as the received signal strength indicator (RSSI).

Although position estimations can be aided by map matching, positioning generally does not provide information about the physical characteristics of a venue, such as the presence of walls, partitions or other barriers that might prevent contact between two users that are otherwise in proximity. Correspondingly, in addition or alternatively to map matching, contact tracing according to the techniques of this disclosure can employ map information to accurately characterize traversable areas of the venue and obstacles that can prevent contact. A map is a global representation of all the elements/objects in the real-world that might affect the measurements logged by the sensors. A map can be either static or dynamic depending on whether static only or static and dynamic objects are represented in the map. Two well-known forms of maps include Location-based maps and feature-based maps.

In a location-based map, the map is represented as a set of objects in set m, where the $i^{th}$ object denoted by $m_i = m_{ix,iy,iz}$ in set m, is a 3D location in the map. Here, $m_{ix,iy,iz}$ is the cartesian coordinates represented by the $i^{th}$ element. Each location-object can contain other attributes describing the object. A distinctive characteristic of location-based maps is that the list of objects in the set m are indexed by their location instead of any other attribute. The main advantage of location-based maps is that every location in the map is represented, hence, the map has a full description of empty and non-empty locations in the map. A well-known example of Location-based maps is an Occupancy Grid Map (OGM), where the real world is discretized into squares (in the case of 2D maps) or cubes (in the case of 3D maps). The objects in the OGM map are the locations of the center-point of the squares/cubes, where each location-object might have several attributes. For example, one attribute could reflect whether the squares/cubes are occupied or empty (alternatively this attribute could reflect whether the squares/cubes are occupied, empty or unmapped), another attribute could contain the expected measurements vector of a specific sensor at the current location-object.

In a feature-based map, the map is represented as a set of objects in a set m, where the $i^{th}$ object denoted by $m_i$ is a specific feature-object in the map. In other words, a feature-based map is a collection of objects that somehow represent certain features in the environment. These objects usually have several attributes including the location of the object. A distinctive characteristic of a feature-based map is that only selective locations of the environment are represented in m. Feature-based maps can either be sparse or dense depending on the number of feature-objects across the map. Moreover, the feature-objects can be uniformly distributed (or any other distribution) across different locations in a map, or feature-objects can be congested in specific locations. Finally, the uniqueness of each of the feature-objects is another characteristic of a feature-map. These characteristics affect how useful the feature-map can be used for localization purposes. A feature-based map that consists of dense, unique and uniformly distributed feature-objects (across locations in a map) are generally favorable characteristics for localization systems.

Figure 6A:
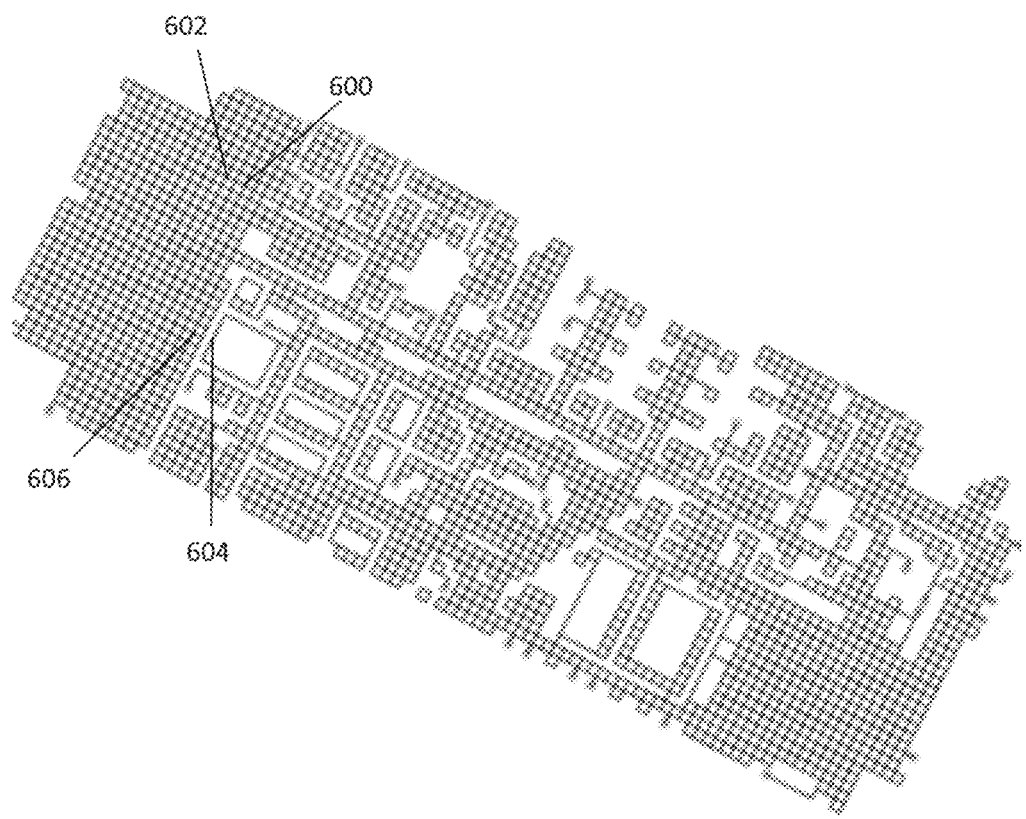
FIGS. 6A and 6B are schematic representations of map information used for establishing contact tracing according to an embodiment.
Figure 6B:
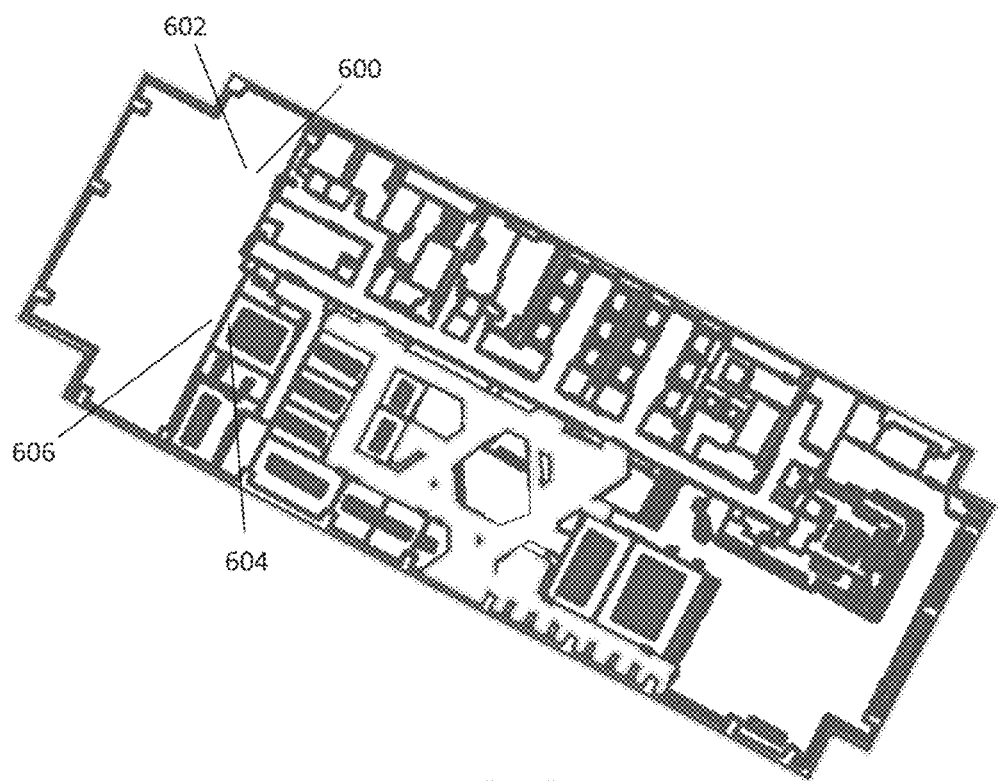

On-line indoor/outdoor map service providers may provide web Application Programming Interfaces (APIs) to access their map database. Accordingly, the corresponding APIs from the map provider may be used to obtain map information for an area encompassing the user's current location. Particularly notable examples of venues that may have corresponding map information include indoor environments such as office buildings, hospitals, malls, conference centers, exhibitions, retail stores and the like. This map information may be preprocessed to facilitate its use. For example, the information may be decoded to extract the necessary map data used for techniques of this disclosure using the APIs and converted into a unified format such as the Geographic Javascript Objective Notation (GeoJson) format, although xml files, binary files and others may be used. The converted map data can then be saved in the local storage for future use. The decoding and conversion may be performed by external resources and delivered in any suitable manner for use during the contact tracing routines of this disclosure. Preprocessing the map information may include segregating it into traversable and non-traversable regions. For example, corridors represent an important class of traversable regions in typical indoor environments. For the purposes of map matching, it will be appreciated that some map entities may provide inherent position information, such as elevators, escalators, stairs that may be associated with level change scenarios or conveyors that may allow the assumption of heading or other position information. The locations of the entrances and exits to the background map entity, as well as doors or other entrances/exits to foreground entities may also be used. Still further, the direction of the entrances/exits may also be used. In a multi-level venue, the height of each level may be used with sensor information indicating changes in elevation to help determine when a level change scenario may exist. Map information may be presented geometrically using polygons in a vector map and/or with connected links and nodes as a grid map. A grid map may enhance the geometric aspects of map matching as well as providing topological aspects. For example, the topological information from the map may be also applied to improve the reliability and the accuracy. As an illustration, a retail store map may be readily divided into structured areas and non-structured areas. Non-structured areas, such as open space, isolated booths and the like, may benefit from geometric based map matching algorithms techniques as described above. However, structured areas, such as aligned shelves, booths and similar features may be abstracted as connected links and nodes to be used in a grid based map. Either or both a polygon based geometric or vector map and a grid map can be employed as warranted for map matching when estimating positions for portable devices 100-1-100-n and/or applied to refine contact determinations. For example, a retail store map can be readily divided into structured areas and non-structured areas. At those non-structured areas such as open spaces, isolated booths and the like, geometric based techniques described above may be applied. Alternatively or in addition, at structured areas such as aligned shelves or booths, the geometric and topological information may be represented by a grid map. When a grid map is available, a weighted topological algorithm based on the correlation between the trajectory of the user and the topological features may be applied As one illustration, FIGS. 6A and 6B represent a venue using a grid map and a vector map respectively. In both maps, a comparison is shown for positions between two devices to help demonstrate how understanding the physical characteristics of the venue may be used to refine contact determinations. In both views, positions 600 and 602 are separated by approximately the same distance as positions 604 and 606. However, positions 600 and 602 are within a common, unstructured area and their distance is sufficiently close that a contact can be determined while positions 604 and 606 are separated by a wall and it may be determined that no contact occurred despite the physical proximity.

From the above discussion, one embodiment of contact determination uses the position estimations for each portable device to determine the number of users per unit area of the venue, such as through density filter 136 as implemented by server 126. Using a suitable threshold as a contact parameters, once a given density is exceeded, it may be determined that contact between the affected users has occurred. For example, machine learning techniques may be employed by using training data of position estimations for scenarios in which infection is likely to occur and scenarios in which infection is unlikely to occur. Then, the developed algorithms may be applied to actual user position estimations to determine whether density is sufficient to infer contact. Alternatively or in addition, proximity may be evaluated based on the estimated positions of the users, such as through proximity detector 138 of server 126. As desired, any suitable distance calculation may be employed, such as using the Haversine Distance (the great circle distance between points on a sphere) between users to identify users close enough for contact to have occurred.

Figure 7:
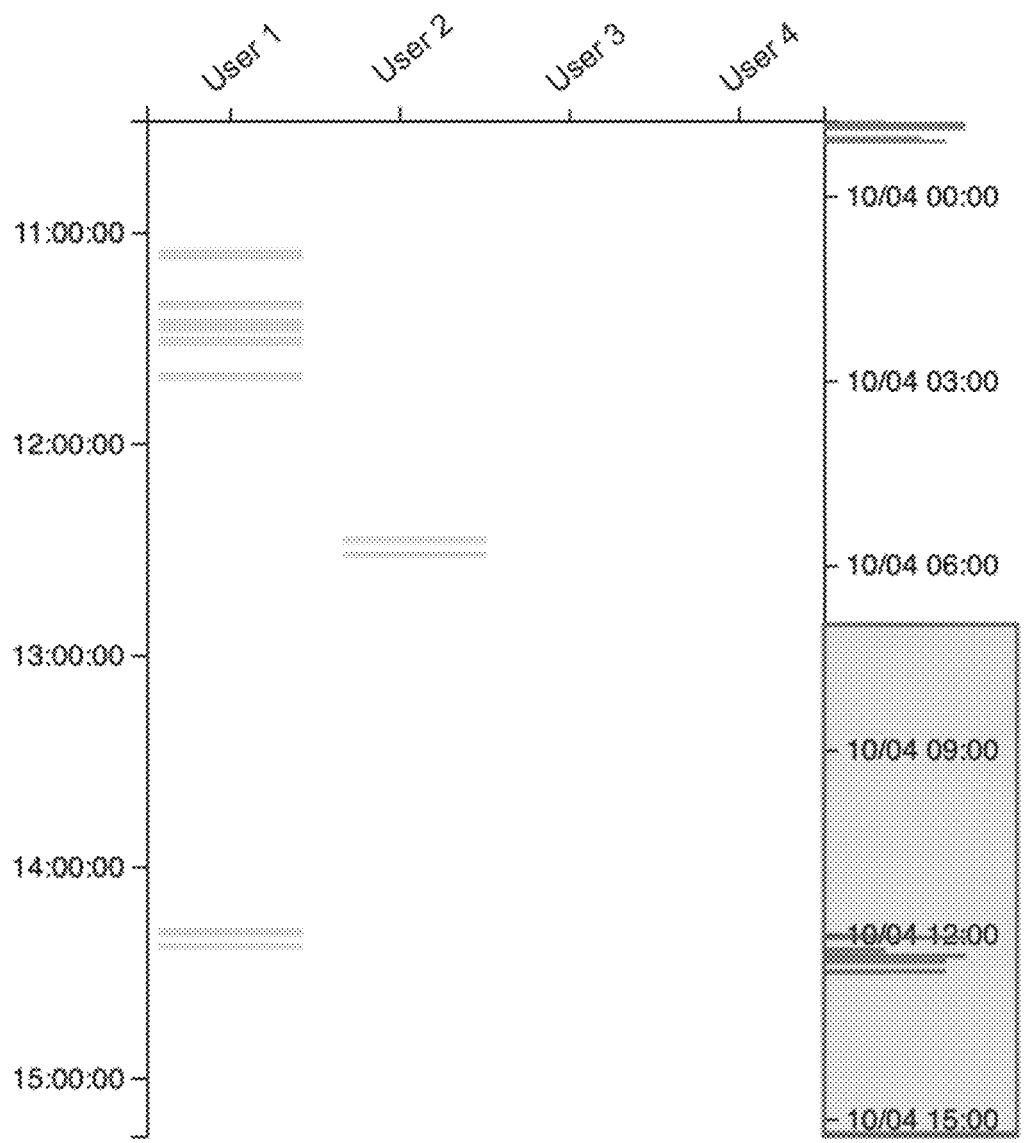
FIG. 7 is a schematic representation of area presence evaluation for a confined area according to an embodiment.

In addition to refining the determination of contemporaneous contacts under the scenarios discussed above, map information may also be used for area presence evaluation. Together with the zone information of FIG. 3, map information can identify aspects of the venue for use in determining the potential for infectious transmission through common interactions with assets such as surfaces or equipment within the venue or presence in a confined area, such as through area presence evaluator 140 of server 126. To help illustrate, FIG. 7 schematically illustrates a timeline for user presence within a confined area and it should be appreciated that similar representations can be made for interactions with assets. The shaded bars under User 1 and User 2 indicate the respective presence of each user within a given confined area, which may be determined based on the history of the position estimates for the portable devices associated with each. The right axis represents a selected time range for generating a report with a histogram of the data showing the data distribution over the entire range. As shown, User 1 occupied the area between 11:00 and 12:00 and between 14:00 and 15:00, while User 2 occupied the area between 12:00 and 13:00. Since the relative time information is available, contact can be determined using appropriate time interval thresholds for the expected viability of an airborne infectious agent. Similarly, appropriate thresholds may be employed when considering the viability of the infectious agent on surfaces, equipment or other assets. For example, once it is known that User 1 is contagious, User 2's occupancy may be within a time threshold to determine a contact has occurred. On the other hand, if User 2 was found to be contagious, the previous occupancy from 11:00-12:00 of User 1 can be ignored and the subsequent occupancy from 14:00-15:00 may be sufficiently removed from the relevant time threshold so that no contact is determined.

Figure 8:
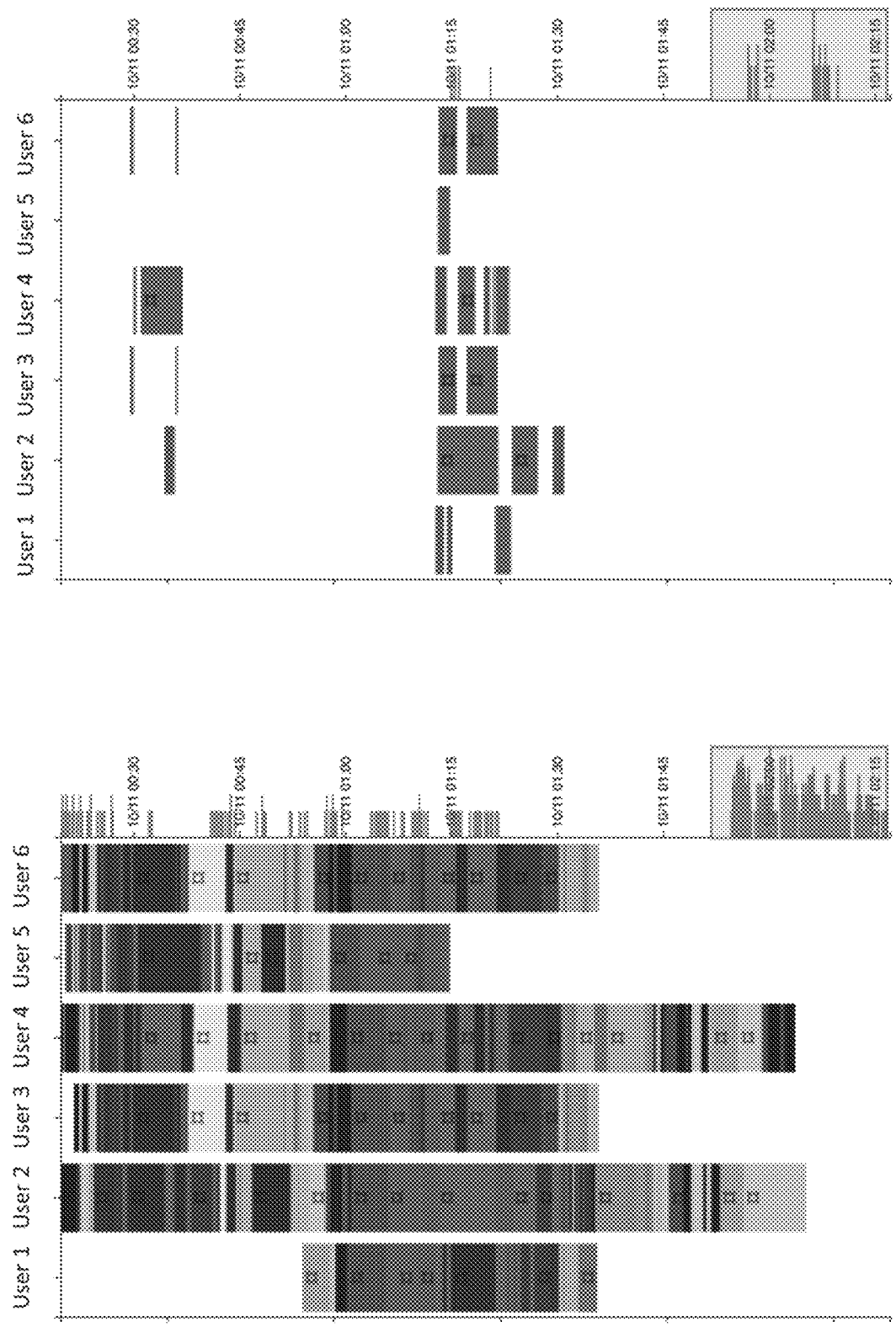
FIG. 8 is a schematic representation of area presence evaluation for multiple assets/areas according to an embodiment.

A more complex scenario is schematically depicted in FIG. 8, in which the left side view shows the presence of multiple users with respect to multiple areas/assets, each denoted by a different shade. This situation is common in venues such as an office that may have many surfaces or other assets that may be subject to common interaction among the users as well as multiple confined areas that may be occupied by multiple users, such as meeting rooms, cafeterias or the like. Correspondingly, the right side view shows a single asset/confined area selection that may be used to determine which users were potentially subject to common interaction. For both views, the right axis represents a selected time range for generating a report with a histogram of the data showing the data distribution over the entire range. For example, between the first period of 00:30 and 00:45, Users 2, 3, 4 and 6 commonly interacted with the asset in the same time frame. Similarly, between a second period of 01:15 and 01:30, Users 1-6 all were in common interaction. In addition to the potential for contemporaneous exposure during each of these two intervals, depending on the characteristics of the infectious agent and the corresponding time interval threshold, contact can also be determined between Users in the first period and Users in the second period. Notably, without the history of position estimations and the understanding of the physical characteristics of the venue provided by the map information, such refined contact determinations would not be possible. As one illustration, a suitable time interval threshold may be applied when determining whether sufficient time has elapsed between the occupancy of a confined area by a first User or group of Users and subsequent occupancy a second User or group of Users based on air circulation, expected viability of the infectious agent or any other relevant criteria.

Figure 9:
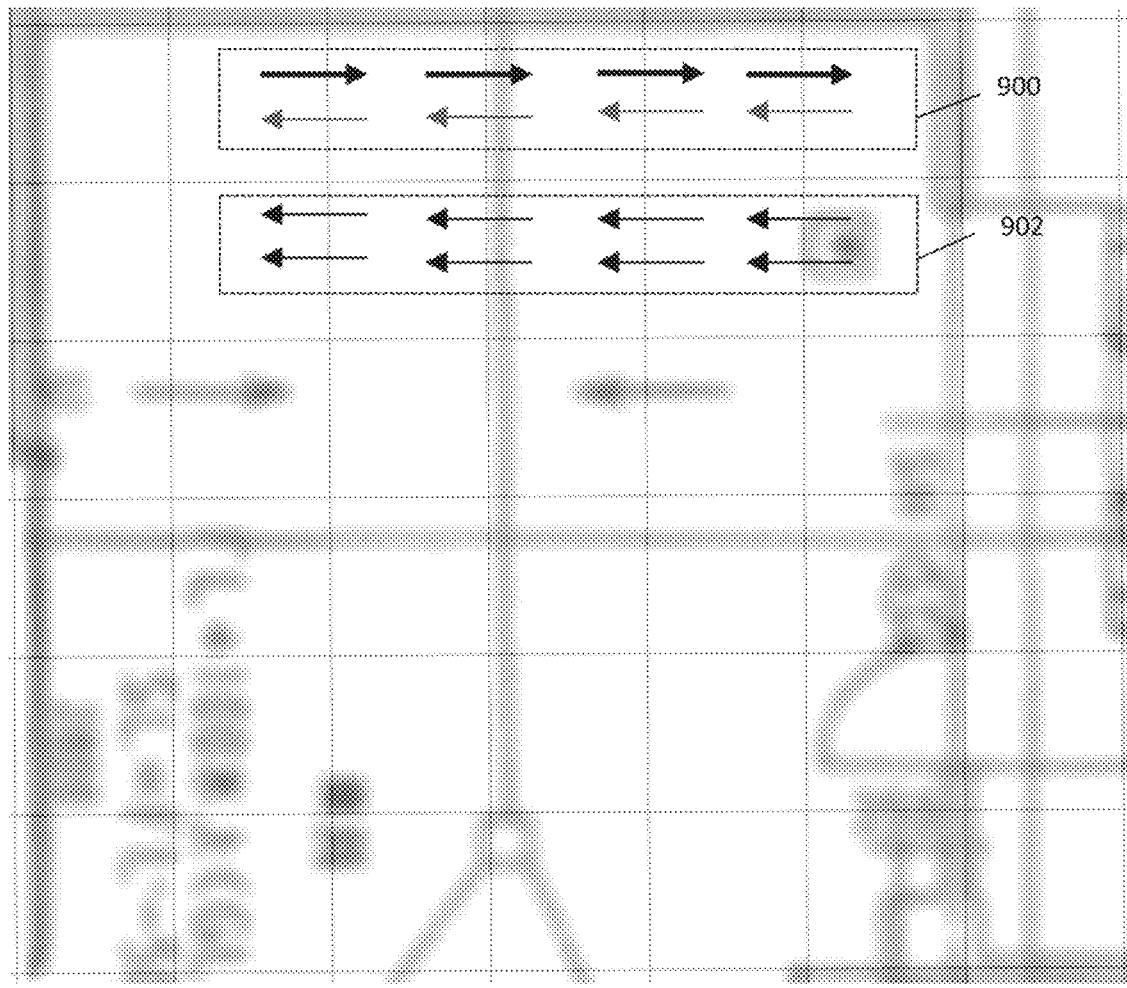
FIG. 9 is a schematic representation of determining cross traffic flow according to an embodiment.

Another usage of zone and map information relates to the dynamic occupancy of the venue. As discussed above, tracking the history of position estimations for each user allows for the determination of trajectories within the venue that can be used for determining contacts. For example, a common mitigation strategy involves constraining corridors, hallways, other paths or portions of them to specific directions in order to reduce the potential for contact between users traversing them. To help illustrate, FIG. 9 schematically depicts a detailed view of one portion of a venue in which segment 900 is reserved for travel in the left to right direction and segment 902 is correspondingly reserved for travel in the opposite direction, right to left. As long as users maintain the intended directionality, as indicated by the top arrows in segment 900 and both top and bottom arrows in segment 902, cross traffic is reduced and the potential for contact is likewise reduced. However, when a user does not conform and travels in the opposite direction as indicated by the bottom arrows in segment 900, a contact may be determined.

Figure 10:
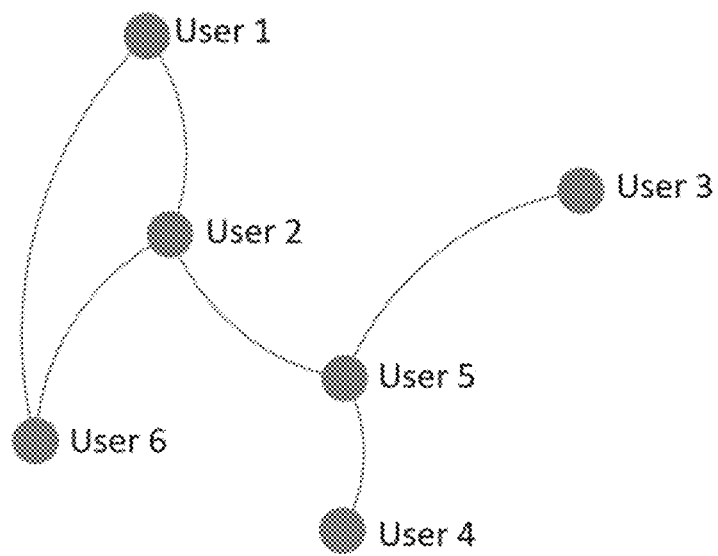
FIG. 10 is a schematic representation of indirect contacts according to an embodiment.

Although some of the embodiments discussed above have concerned the common interaction of two or more users with a surface, asset or collocation in a confined area, it should also be appreciated that contact between two users can also be determined based on common interaction with another user. Notably, diseases can spread through communities though the type of direct contact discussed above but the techniques of this disclosure can identify indirect contacts as well. Using the history of position estimations for each user, all contacts with different users can be traced. Linking together this information with respect to a common user or place may be used to determine users who are at risk. For example, FIG. 10 schematically depicts interactions between multiple users, with lines denoting direct contacts. Here, even though not all users come into direct contact, common interactions may still create indirect contacts. In one scenario, if it is determined User 1 is infected, all potential contacts should be evaluated. Particularly, User 2 and User 6 have come into direct contact with User 1, but User 5 has indirect contact through User 2 and Users 3 and 4 correspondingly have indirect contact through User 5. As warranted, the different degrees of indirect contact can be used in the determination of likelihood of disease spread.

Figure 11A:
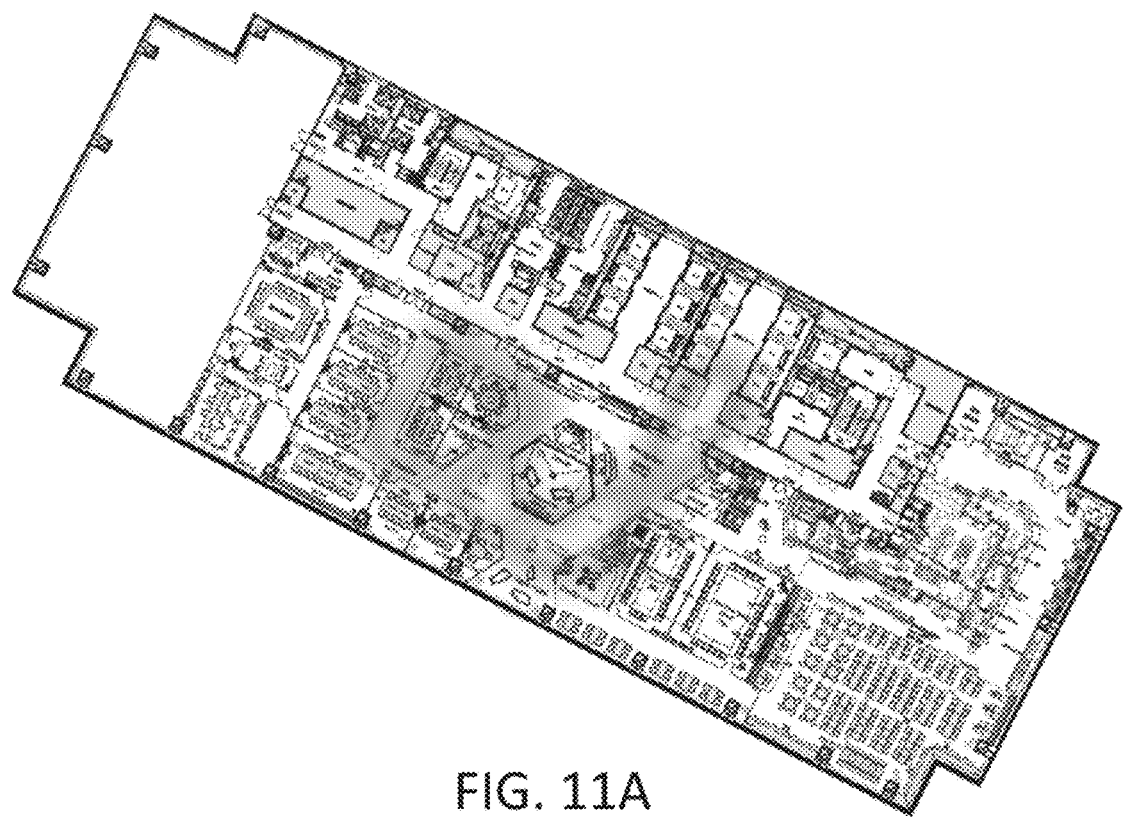
FIGS. 11A and 11B are schematic representations of heat maps according to an embodiment.
Figure 11B:
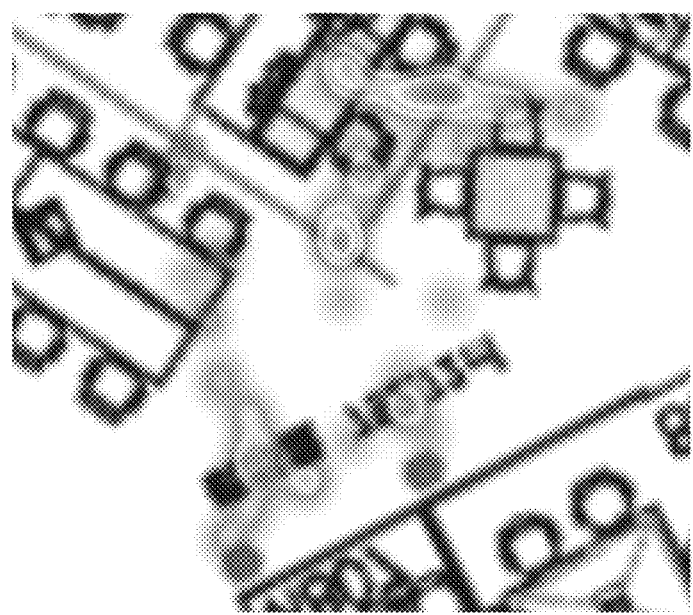

Another aspect of the contact tracing routines using map information relates to the heat maps, such as provided by heat map generator 142 of server 126. A heat map uses shading to indicate the locations and amount of time spent in those locations for a given user. For example, FIG. 11A schematically depicts the presence of a user within the venue. Any suitable time interval, such as hours, day, weeks or longer may be used to represent the user's exposure to various locations within the venue. Again, the interval can be adjusted as warranted depending on the characteristics of the infectious agent being tracked. As will be appreciated, this information is useful once it has been determined a user is infectious because the heat map can then be used to identify which portions of the venue need to be sanitized. Targeting only the places the infectious user has been allows for a more expedient response by focusing efforts on the needed areas while allowing unaffected areas to operate normally. Further, heat maps can also be used when making the contact determination. For example, FIG. 11B shows a detail of the venue from FIG. 11A, with heat maps for multiple users superimposed upon each other. This depiction is of a group of users meeting, such that contact may be inferred among them.

From the above, it will be appreciated that the techniques of this disclosure involve contact tracing based on estimating positions of users in a venue rather than simply relying on relative contemporaneous distances between users. Moreover, employing map information allows for contact determinations based on the physical characteristics of the venue rather than proximity alone. Still further, maintaining a history of position estimates over time permits the determination of contact between users not possible based on contemporaneous proximity alone. Contact may be determined by either or both of actual distance between estimated positions or a density of users per unit area. As such, the techniques are not limited to a particular number of users and position estimations can access more information than available from peer to peer ranging techniques. From the above discussion, it will be appreciated that this enables a more accurate determination of contacts and consequently a greater chance for evaluating the likelihood of disease spread.

Contemplated Embodiments

The embodiments and techniques described above may be implemented in software as various interconnected functional blocks or distinct software modules. This is not necessary, however, and there may be cases where these functional blocks or modules are equivalently aggregated into a single logic device, program or operation with unclear boundaries. In any event, the functional blocks and software modules implementing the embodiments described above, or features of the interface can be implemented by themselves, or in combination with other operations in either hardware or software, either within the device entirely, or in conjunction with the device and other processor enabled devices in communication with the device, such as a server.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and described or portions thereof, it being recognized that the disclosure is defined and limited only by the claims that follow.

What is claimed is:

1. A method for establishing contact tracing for a group of users within a venue, the method comprising:
    a) estimating position information in the venue for each user over a period of time based at least in part on data from a portable device associated with each user, wherein estimating position information comprises determining a position for each device of each user at a plurality of given instants;
    b) establishing at least one contact parameter, wherein the at least one contact parameter is adjustable; and
    c) determining contact between at least two users of the group of users during the period of time by temporally aligning the determined positions and based at least in part on the at least one contact parameter.

2. The method of claim 1, wherein the at least one contact parameter is any one or any combination of at least one threshold distance for inferring contact and at least one threshold time interval for inferring contact.

3. The method of claim 1, wherein determining a contact between the at least two users is further based on a density computed using machine learning.

4. The method of claim 1, wherein determining a contact between the at least two users is further based on a Haversine distance between the two users.

5. The method of claim 1, wherein determining a contact between the at least two users is further based on common interaction with an asset within the venue.

6. The method of claim 1, wherein determining a contact between the at least two users is further based on common interaction with another user of the group of users.

7. The method of claim 1, further comprising obtaining map information for the venue, wherein determining contacts between the at least two users is based at least in part on the map information.

8. The method of claim 7, wherein determining contacts between the at least two users is based at least in part on a physical characteristics of the venue derived from the map information.

9. The method of claim 7, further comprising identifying at least one confined area, wherein determining a contact between the at least two users is further based on collocation of the two users in the identified confined area.

10. The method of claim 1, wherein the estimated position information is based at least in part on motion sensor data from at least one of the portable devices.

11. The method of claim 10, wherein the estimated position information is further based at least in part on at least one of:
    i) a magnetic fingerprint;
    ii) a Wi-Fi fingerprint;
    iii) Bluetooth proximity;
    iv) a Bluetooth fingerprint;
    v) map matching; and
    vi) other absolute positioning systems.

12. The method of claim 1, wherein determining a contact between the at least two users is further based on a ranging proximity between the portable devices associated with the two users.

13. The method of claim 12, wherein the ranging proximity is based on Bluetooth Low Energy communication.

14. The method of claim 1, wherein determining a contact between the at least two users is further based on heatmaps for each of the at least two users as determined from the position information.

15. The method of claim 1, wherein determining a contact between the at least two users is further based on trajectories of each of the two users as determined from the position information.

16. The method of claim 15, wherein the trajectories of the at least two users indicates cross traffic flow.

17. The method of claim 1, further comprising estimating a probability of disease spread between two users for which a contact has been determined.

18. A system for establishing contact tracing for a group of users within a venue, the system comprising:
    a) a portable device associated with each user, wherein each portable device comprises at least one processor configured to estimate position information based at least in part on data from the portable device, wherein estimating position information comprises determining a position for the portable device at a plurality of given instants; and
    b) at least one remote processor configured to:
        i) receive the estimated position information in the venue for each user over a period of time;
        ii) establish at least one contact parameter, wherein the at least one contact parameter is adjustable; and
        iii) determine contact between at least two users of the group of users during the period of time by temporally aligning the determined positions and based at least in part on the at least one contact parameter.

19. The system of claim 18, wherein the at least one contact parameter is any one or any combination of at least one threshold distance for inferring contact and at least one threshold time interval for inferring contact.

20. The system of claim 18, wherein the estimated position information is based at least in part on motion sensor data.

21. The system of claim 18, wherein the estimated position information is further based at least in part on at least one of:

i) a magnetic fingerprint;
ii) a Wi-Fi fingerprint;
iii) Bluetooth proximity;
iv) a Bluetooth fingerprint;
v) map matching; and
vi) other absolute positioning systems.

22. The system of claim 18, wherein each portable device associated with at least two users further comprises a ranging module, such that determining a contact between the at least two users is further based on a ranging proximity.

23. The system of claim 18, wherein the at least one remote processor is configured to receive map information for the venue, wherein determining contact between at least two users is further based on the map information.

24. A system for establishing contact tracing for a group of users within a venue, the system comprising:
   a) a portable device associated with each user; and
   b) at least one remote processor configured to:
   i) estimate position information in the venue for each user over a period of time based at least in part on data from the portable device of each user, wherein estimating position information comprises determining a position for each device of each user at a plurality of given instants;
   ii) establish at least one contact parameter, wherein the at least one contact parameter is adjustable; and
   iii) determine contact between at least two users of the group of users during the period of time by temporally aligning the determined positions and based at least in part on the at least one contact parameter.

25. The system of claim 24, wherein the at least one contact parameter is any one or any combination of at least one threshold distance for inferring contact and at least one threshold time interval for inferring contact.

26. The system of claim 24, wherein the estimated position information is based at least in part on motion sensor data.

27. The system of claim 24, wherein the estimated position information is further based at least in part on at least one of:
   i) a magnetic fingerprint;
   ii) a Wi-Fi fingerprint;
   iii) Bluetooth proximity;
   iv) a Bluetooth fingerprint;
   v) map matching; and
   vi) other absolute positioning systems.

28. The system of claim 24, wherein each portable device associated with at least two users further comprises a ranging module, such that determining a contact between the at least two users is further based on a ranging proximity.

29. The system of claim 24, wherein the at least one remote processor is configured to receive map information for the venue, wherein determining contact between at least two users is further based on the map information.

* * * * *